United States Patent
Hoernig (10) Patent No.: US 10,820,873 B2
(45) Date of Patent: Nov. 3, 2020

(54) METHOD, SYSTEM, AND COMPUTER PROGRAM PRODUCT FOR GENERATING CONTRAST-ENHANCED IMAGE DATA OF BREAST TISSUE

(71) Applicant: SIEMENS HEALTHCARE GMBH, Erlangen (DE)

(72) Inventor: Mathias Hoernig, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 800 days.

(21) Appl. No.: 15/259,290

(22) Filed: Sep. 8, 2016

(65) Prior Publication Data

US 2017/0065241 A1   Mar. 9, 2017

(30) Foreign Application Priority Data

Sep. 8, 2015   (DE) .................. 10 2015 217 141

(51) Int. Cl.
*A61B 6/00*   (2006.01)
*A61B 6/02*   (2006.01)

(52) U.S. Cl.
CPC ............ *A61B 6/502* (2013.01); *A61B 6/025* (2013.01); *A61B 6/481* (2013.01); *A61B 6/482* (2013.01);
(Continued)

(58) Field of Classification Search
CPC ....... A61B 6/502; A61B 6/5223; A61B 6/504; A61B 6/482; A61B 6/5235; A61B 6/481; A61B 6/025; A61B 6/5205; A61B 6/52
See application file for complete search history.

(56) References Cited

U.S. PATENT DOCUMENTS 7,760,924 B2   7/2010   Ruth et al.
2009/0208085 A1*   8/2009   Muller ................. G06T 11/006
                                                                    382/131
(Continued)

FOREIGN PATENT DOCUMENTS

DE   102011087128   *  5/2013   ............. A61B 6/481
DE   102011087128 A1   5/2013
(Continued)

OTHER PUBLICATIONS

Muller, S., Dromain, C., Balleyguier, C., Patoureaux, F., Puong, S., & Bouchevreau, X. (2010). Contrast enhanced digital mammography (CEDM): from morphological to functional mammography. Poster No. C-0300, ECR. pp. 1-20 (Year: 2010).*

*Primary Examiner* — Oommen Jacob
*Assistant Examiner* — Shahdeep Mohammed
(74) *Attorney, Agent, or Firm* — Laurence Greenberg; Werner Stemer; Ralph Locher (57) ABSTRACT

Contrast-enhanced image data of breast tissue to be examined is generated. First two-dimensional contrast-agent-influenced x-ray projection data of the breast tissue are acquired at a first x-ray beam energy and a two-dimensional image data record is generated on the basis of the first two-dimensional x-ray projection data. Second two-dimensional contrast-agent-influenced x-ray projection data are acquired from different projection angles at a second x-ray beam energy that differs from the first x-ray beam energy and a three-dimensional tomosynthesis image data record of the breast tissue is reconstructed from the detected second two-dimensional x-ray projection data. Subsequently, a two-dimensional synthetic mammogram is calculated on the basis of the three-dimensional tomosynthesis image data record and a two-dimensional dual-energy mammogram is established by subtracting the image data of the synthetic mammogram from the image data of the two-dimensional image data record.

14 Claims, 4 Drawing Sheets

(52) U.S. Cl.
CPC ............ *A61B 6/504* (2013.01); *A61B 6/5205* (2013.01); *A61B 6/5223* (2013.01); *A61B 6/5235* (2013.01)

(56) References Cited

U.S. PATENT DOCUMENTS

| | | | | |
|---|---|---|---|---|
| 2011/0019891 A1* | 1/2011 | Puong | ............ | A61B 6/405 382/131 |
| 2012/0134464 A1* | 5/2012 | Hoernig | ............ | A61B 6/025 378/22 |
| 2012/0238870 A1* | 9/2012 | Smith | ............ | A61B 6/025 600/431 |
| 2014/0072096 A1 | 3/2014 | Hoernig | | |
| 2014/0376691 A1 | 12/2014 | Hoernig | | |
| 2016/0140749 A1* | 5/2016 | Erhard | ............ | G06T 15/205 345/424 |

FOREIGN PATENT DOCUMENTS

| | | | | |
|---|---|---|---|---|
| DE | 102012215997 A1 | 3/2014 | | |
| DE | 102013211547 B3 * | 5/2014 | ............ | G06T 11/006 |
| DE | 102013211547 B3 | 5/2014 | | |

* cited by examiner

FIG 1
PRIOR ART

METHOD, SYSTEM, AND COMPUTER PROGRAM PRODUCT FOR GENERATING CONTRAST-ENHANCED IMAGE DATA OF BREAST TISSUE

CROSS-REFERENCE TO RELATED APPLICATION

This application claims the priority, under 35 U.S.C. § 119, of German patent application DE 10 2015 217 141.8, filed Sep. 8, 2015; the prior application is herewith incorporated by reference in its entirety.

BACKGROUND OF THE INVENTION

Field of the Invention

The invention relates to a method for generating contrast-enhanced image data of breast tissue to be examined. Furthermore, the invention relates to an image data generation system.

Figure 1:
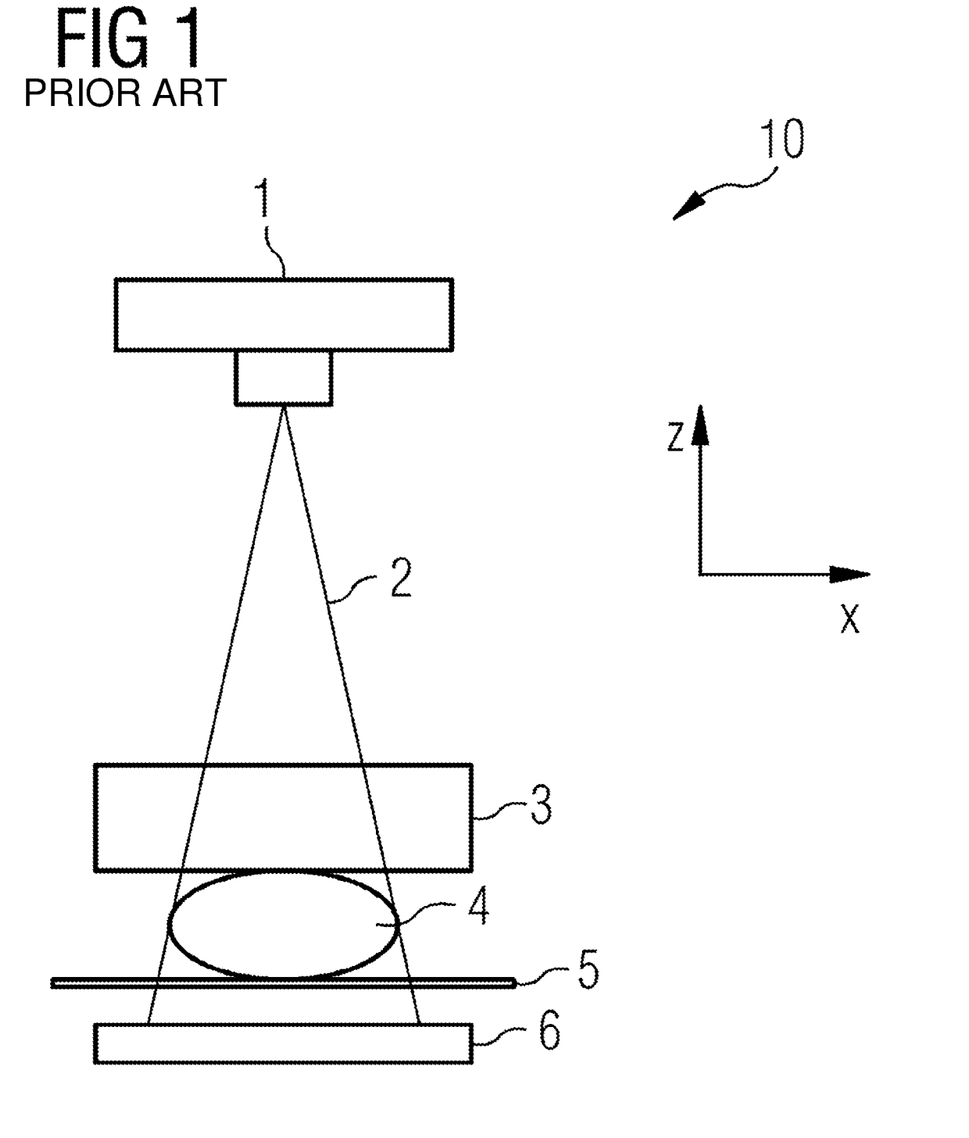
FIG. 1 shows a conventional mammography system for two-dimensional x-ray image recording of a breast.

Mammography continues to play an important role in the early detection of breast cancer. In conventional mammography, an x-ray recording of the female breast is created. The x-ray radiation employed in the process is soft radiation with an energy of approximately 25 to 35 keV. For the purposes of detecting the x-ray radiation, use is made of direct digital detectors and indirect digital detectors to detect the emitted x-ray radiation. Direct digital detectors convert the x-ray radiation directly into an electrical signal. By contrast, indirect digital detectors convert the x-ray radiation into visible light first, the latter subsequently being converted into an electrical signal. The x-ray recordings are observed at a special mammography findings station, which comprises one or two grayscale monitors by means of which the x-ray images are represented as an image. An exemplary arrangement for two-dimensional mammography is shown in FIG. 1.

A problem arising in conventional two-dimensional mammography is that pathological changes in the tissue are often covered by the superposition of various tissue structures, and so these are not identified. Attempts are made to compensate this problem by recording the breast from two different angles, "craniocaudal" and "mediolateral oblique," i.e., once at a perpendicular and once at a 45° angle thereto.

Figure 2:
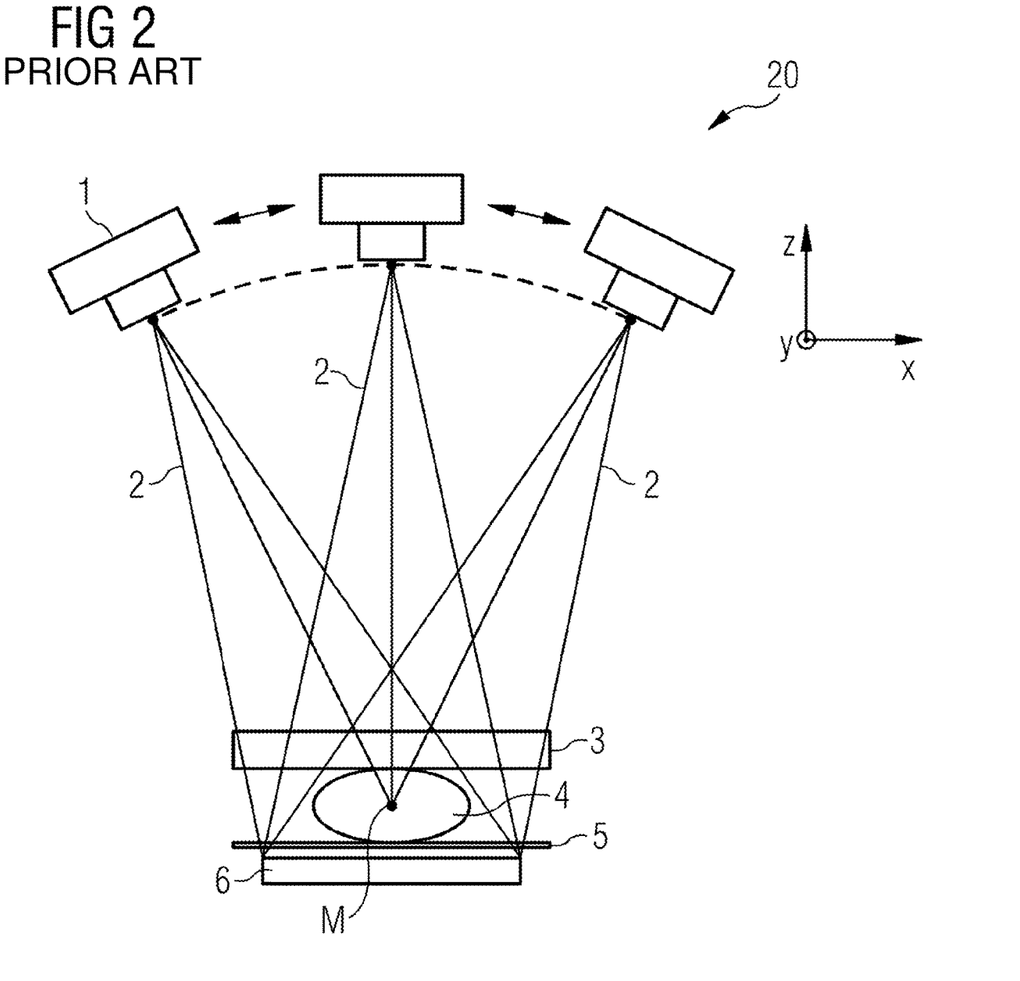
FIG. 2 shows a conventional tomosynthesis system for three-dimensional x-ray image recording of a breast.

3D breast tomosynthesis offers an imaging method in which the breast is recorded from many different angles. By way of example, recordings are recorded at angles of 15 to 50 degrees. In total, between 9 and 25 recordings are recorded from different angles with a low dose and a high acceleration voltage such that the overall dose approximately corresponds to that of a conventional two-dimensional mammography recording. Images for individual layers of the breast tissue are calculated from the detected projection data. By way of example, the method of filtered back projection is used for reconstructing a three-dimensional image of a region to be examined from the detected projection data. For diagnosis purposes, the resultant three-dimensional image can be observed slice-by-slice. Since slices above and below the respective slice selected for viewing can be masked during the findings, changes in the tissue are more easily identified. A system for three-dimensional imaging of breast tissue with the aid of tomosynthesis is depicted in FIG. 2.

In order to generate the findings, a two-dimensional mammography recording is additionally also required. However, the creation of a two-dimensional mammography recording in addition to the tomosynthesis is a strain on the patient because the x-ray dose of the patient would be increased in such a case. Therefore, so called synthetic two-dimensional mammography is often applied for this case, where a two-dimensional image is back-calculated from the data record of the three-dimensional tomosynthesis.

In order to be able to eliminate tissue structures which could cover lesions from the image representation, a high-energy recording, followed by a low-energy mammography recording while maintaining the breast compression, is typically carried out after a preceding contrast agent administration in the case of contrast-enhanced dual-energy mammography (CEDEM). Subsequently, a recombined result image is created after registration and a weighted subtraction, said result image substantially depicting regions in which the contrast agent has accumulated in a particularly well visible manner. Expressed differently, the different x-ray beam energies are selected in such a way that the value of the lower energy lies below the energy value of the absorption edge of the employed contrast agent for the x-ray radiation and the value of the higher energy lies above the energy value of the absorption edge of the employed contrast agent for x-ray radiation. By way of example, the K absorption edge for x-ray radiation for the iodine contrast agent, also abbreviated to x-ray edge below, lies at 33.17 keV. Such a selection of the energy values for the x-ray radiation for the different recordings leads to the structures penetrated by the contrast agent, e.g. lesions, being detected more clearly in the breast tissue in imaging with x-ray radiation with a higher energy than when imaging with x-ray radiation with a lower energy. If a difference image is generated from the two images, an image of the lesions without interfering or covering background structures or tissue structures is obtained, which simplifies finding of the lesions.

The calculation of a recombined dual-energy mammogram from 3D breast tomosynthesis (CEDET) is described in my earlier patent application US 2014/0072096 A1 and its counterpart German published patent application DE 10 2012 215 997 A1. However, that method also still requires a high-energy tomosynthesis recording and a low-energy tomosynthesis recording, as a result of which the dose exposure of the patient is increased.

SUMMARY OF THE INVENTION

It is accordingly an object of the invention to provide a method and a device for generating contrast-enhanced image data in the context of breast tissue examination which overcomes the above-mentioned and other disadvantages of the heretofore-known devices and methods of this general type and which provides for a method with low exposure in terms of dose for the patient, and which unifies the advantages of three-dimensional breast tomosynthesis with the advantages of two-dimensional dual-energy mammography.

In other words, the objects of the invention are achieved a method for generating contrast-enhanced image data of breast tissue to be examined, as claimed, by way of an image data generation system, as claimed, and by way of an associated computer program product.

In the method according to the invention for generating contrast-enhanced image data of breast tissue to be examined, first two-dimensional contrast-agent-influenced x-ray projection data of the breast tissue to be examined are detected at a first x-ray beam energy. In this case, contrast-agent-influenced x-ray projection data should be projection data which were recorded in the presence of a contrast agent.

By way of example, the detected x-ray projection data can originate from a database or, alternatively, be detected directly during a measuring process.

A two-dimensional image data record is generated on the basis of the detected first two-dimensional x-ray projection data. This image data record is also referred to as mammogram or mammography image.

Additionally, in the method according to the invention, second two-dimensional contrast-agent-influenced x-ray projection data are detected from a plurality of different projection angles at a second x-ray beam energy that differs from the first x-ray beam energy. The detected second x-ray projection data can also originate from e.g. a database or, alternatively, be detected directly during a measuring process. After projections are detected from different angles, a three-dimensional tomosynthesis image data record of the breast tissue to be examined is generated from the detected second two-dimensional x-ray projection data. For the purposes of reconstructing a three-dimensional image data record from the projection images detected from various angles, use can be made e.g. of the method of filtered back projection. Furthermore, a two-dimensional synthetic mammogram is calculated on the basis of the three-dimensional tomosynthesis image data record. By way of example, such a calculation of a two-dimensional synthetic mammogram is known from U.S. Pat. No. 7,760,924 B2. The reason for not simply using an individual projection of the tomosynthesis projection data, for example, at an angle of 0°, as two-dimensional synthetic mammogram can be found in the fact that the individual projections were recorded with a very low dose during the tomogram recording, for example with 1/25 of the overall dose. As a consequence of the low dose, the individual recordings are strongly afflicted by noise and do not offer good resolution.

Finally, a two-dimensional dual-energy mammogram is established by subtracting the image data of the synthetic mammogram from the image data of the two-dimensional image data record. A dual-energy mammogram should be understood to mean a mammography representation which arose by subtraction of two mammograms, the associated projection data of which were generated with x-ray radiation at different energies. The recording at different energies leads to a different effect of a contrast agent, used for contrasting in the region to be examined, on the image intensity of the two mammograms in the regions in which the contrast agent has accumulated. Since such contrast agents preferably accumulate in the breast at positions at which lesions which may indicate tumors are situated, a different image intensity of the representation of the lesion emerges in the two mammograms, whereas other image regions are imaged the same in the two mammograms. If the image intensities of the two mammograms are subtracted from one another, the image background or bright image regions caused by dense glandular tissue are eliminated and the lesions or tumors become more easily visible.

With the above and other objects in view there is provided, in accordance with the invention, a method of generating contrast-enhanced image data of breast tissue to be examined. The novel method comprises the following steps:
 detecting first two-dimensional contrast-agent-influenced x-ray projection data of the breast tissue to be examined at a first x-ray beam energy;
 generating a two-dimensional image data record based on the first two-dimensional x-ray projection data;
 detecting from a plurality of different projection angles second two-dimensional contrast-agent-influenced x-ray projection data at a second x-ray beam energy that differs from the first x-ray beam energy;
 reconstructing a three-dimensional tomosynthesis image data record of the breast tissue to be examined from the detected second two-dimensional x-ray projection data;
 calculating a two-dimensional synthetic mammogram based on the three-dimensional tomosynthesis image data record;
 establishing a two-dimensional dual-energy mammogram by subtracting the image data of the synthetic mammogram from the image data of the two-dimensional image data record.

With the above and other objects in view there is also provided, in accordance with the invention, an image data generation system, comprising:
 a projection data detection unit configured for detecting first two-dimensional x-ray projection data of breast tissue to be examined at a first x-ray beam energy and for detecting from different projection angles second two-dimensional x-ray projection data at a second x-ray beam energy that differs from the first x-ray beam energy;
 an image data generation unit connected to said projection data detection unit and configured for generating a two-dimensional image data record on a basis of the detected first two-dimensional x-ray projection data;
 a tomosynthesis image data generation unit connected to said projection data detection unit and configured for reconstructing a three-dimensional tomosynthesis image data record of the breast tissue to be examined from the detected second two-dimensional x-ray projection data;
 an evaluation unit connected to said tomosynthesis image data generation unit, said evaluation unit including:
  a computer unit configured to establish a two-dimensional synthetic mammogram on a basis of the three-dimensional tomosynthesis image data;
  a mammogram establishment unit configured to establish a two-dimensional dual-energy mammography representation by subtracting the image data of the synthetic mammogram from the image data of the two-dimensional image data record.

The image data generation system according to the invention has a projection data detection unit for detecting first two-dimensional x-ray projection data of breast tissue to be examined at a first x-ray beam energy and for detecting from different projection angles second two-dimensional x-ray projection data at a second x-ray beam energy that differs from the first x-ray beam energy. Moreover, part of the image data generation system according to the invention is an image data generation unit for generating a two-dimensional image data record on the basis of the detected first two-dimensional x-ray projection data. The image data generation system according to the invention moreover comprises a tomosynthesis image data generation unit for reconstructing a three-dimensional tomosynthesis image data record of the breast tissue to be examined from the detected second two-dimensional x-ray projection data. Moreover, the image data generation system according to the invention has, as a part, an evaluation unit which comprises a computer unit which is configured to establish a two-dimensional synthetic mammogram on the basis of the three-dimensional tomosynthesis image data and a mammogram establishment unit which is configured to establish a two-dimensional dual-energy mammography representation by subtracting the image data of the synthetic mammogram from the image data of the two-dimensional image data record, which was generated on the basis of the first two-dimensional x-ray projection data. Thus, according to the invention, a separate recording of a two-dimensional mammogram with a second x-ray beam energy is dispensed with, wherein, nevertheless, such a dual-energy two-dimensional representation of the breast is generated from a combination of two-dimensional and three-dimensional image data such that the advantages of a dual-energy contrast representation of the breast and the advantages of the tomosynthesis can be used with, at the same time, a lower exposure in terms of dose for the patient.

The primarily important components of the image data generation system according to the invention can be predominantly embodied in the form of software components. In particular, this relates to parts of the projection data detection unit, the image data generation unit, the tomosynthesis image data generation unit and the evaluation unit, and the units such as the computer unit and the mammogram establishment unit comprised thereby. However, in principle, these components can also in part be realized in the form of software-assisted hardware, for example FPGAs or the like, particularly if this relates to particularly fast calculations. Likewise, the required interfaces can be embodied as software interfaces, for example if this only relates to taking over data from other software components. However, they can also be embodied as interfaces set up in the form of hardware, which are actuated by suitable software.

The realization largely in terms of software is advantageous in that even previously used image data generation systems can easily be retrofitted by a software update in order to operate in a manner according to the invention. In this respect, the object is also achieved by a corresponding computer program product comprising a computer program, which is able to be loaded directly into a memory unit of an image data generation system according to the invention, comprising program portions to execute all steps of the method according to the invention when the computer program is executed in the image data generation system.

In addition to the computer program, such a computer program product can, when necessary, comprise additional components such as e.g. documentation and/or additional components, including hardware components such as e.g. hardware keys (dongles, etc.) for using the software.

A computer-readable medium, for example a memory stick, a hard disk drive or any other transportable or securely installed data medium, in which the program portions of the computer program which are readable and executable by a computer unit of the image data generation system are stored in non-transitory form, may serve for transporting to the memory device of the image data generation system and/or for storage at the image data generation system. To this end, the computer unit can have e.g. one or more cooperating microprocessors or the like.

The dependent claims and the subsequent description each contain particularly advantageous refinements and developments of the invention. Here, in particular, the claims of one claim category can also be developed in a manner analogous to the dependent claims of another claim category. Moreover, the various features of different exemplary embodiments and claims can also be combined to form new exemplary embodiments within the scope of the invention.

In one refinement of the method according to the invention for generating contrast-enhanced image data of breast tissue to be examined, a first two-dimensional x-ray image recording at the first x-ray beam energy is carried out for detecting the first two-dimensional x-ray projection data and second two-dimensional x-ray image recordings are carried out from a plurality of different angles at the second x-ray beam energy for detecting the second two-dimensional x-ray projection data. Thus, in the described refinement, the method according to the invention is directly used in an x-ray image recording, wherein the measurement data detected as projection data during the x-ray image recording are then used further for the reconstruction of image data. By way of example, the second two-dimensional x-ray projection data are used in the method according to the invention for the reconstruction of a three-dimensional tomosynthesis image, wherein, for example, the method of filtered back projection can be used as reconstruction method.

In a preferred refinement of the method according to the invention for generating contrast-enhanced image data of breast tissue to be examined, the subtraction of the image data comprises a subtraction of weighted image intensities of the two image data records. The image intensities or intensities of the individual image pixels of the two image data records are preferably weighted in such a way that background structures disappear when subtracting the intensity values of the image data. In this manner, lesions which can, for example, be connected with tumors can be found in a much improved manner. The weighting is dependent on the compression thickness and the tissue density of the breast to be examined.

Preferably, in the method according to the invention for generating contrast-enhanced image data of breast tissue to be examined, the first x-ray beam energy has an energy value which lies above the x-ray edge of a contrast agent applied for contrast enhancement and the second x-ray beam energy has an energy value which lies below the x-ray edge of the contrast agent applied for contrast enhancement. In this variant, a two-dimensional image with a high x-ray beam energy is recorded first and a tomosynthesis image with x-ray radiation with low energy is generated. Advantageously, the tomosynthesis image is generated from x-ray projection data which were recorded with x-ray radiation at a low energy since the image data resulting from the projection data offer an improved detail resolution compared to measurements at a higher energy. This makes it easier to find lesions when examining the three-dimensional image slice-by-slice. As already mentioned, high energy should be understood to mean an energy value which lies above an energy value of the absorption edge, in particular the K absorption edge, of the employed contrast agent. In turn, a low energy should be understood to mean an energy value which lies below an energy value of the absorption edge, in particular the K absorption edge, of the employed contrast agent. In this context, a standard energy recording, in particular, with which mammography is usually carried out should be understood to mean a low energy recording. Energies for such recording usually lie between 23 keV and 35 keV.

Alternatively, the first x-ray beam energy has an energy value which lies below the x-ray edge of a contrast agent applied for contrast enhancement and the second x-ray beam energy has an energy value which lies above the x-ray edge of the contrast agent applied for contrast enhancement. The detail resolution of the three-dimensional representation is slightly lower in this alternative variant. Instead, the contrast of the three-dimensional image in the region of the lesions to be detected is improved since, of course, the value of the second x-ray beam energy in this variant lies above the absorption edge of the applied contrast agent, i.e. the contrast agent can highlight the lesions more clearly during the three-dimensional imaging.

Usually, the first two-dimensional x-ray projection data and the second two-dimensional x-ray projection data are recorded using so-called 1*1 binning. This means that the rastering (screening) of both recordings corresponds to the resolution of the pixels of the employed detector and both recordings are acquired with the same resolution. Alternatively, different resolutions can also be applied to the two recordings, such as e.g. 2*1 binning. Thus, in this case, one recording is carried out with a lower resolution than the other recording. In the case of different resolutions, the detected image matrices are matched to one another by an additional interpolation or extrapolation prior to establishing the two-dimensional dual-energy mammogram by subtracting the image data of the synthetic mammogram from the image data of the two-dimensional image data record. By way of example, the recording with a lower resolution is converted to a grid with a higher resolution by interpolation.

Particularly preferably, the detection of the first two-dimensional x-ray projection data and the detection of the second two-dimensional x-ray projection data is carried out during a single workflow while maintaining a breast compression and/or while maintaining the position of the breast. Maintaining the position of the breast to be examined renders it possible to dispense with the registration of the image data from the three-dimensional image to the image data of the two-dimensional image for the purposes of generating a dual-energy two-dimensional imaging since, of course, the examination of objects ideally remains at the same position during both image recordings and it is also not subject to any geometric change. Additionally, it is naturally also possible to carry out a registration of the image recordings to one another in order to be able to compensate for small deviations in the individual image recordings, for example due to respiratory movements or the like.

In a variant of the method according to the invention for generating contrast-enhanced image data of breast tissue to be examined, which can be applied in a particularly advantageous manner, the detection of the first two-dimensional x-ray projection data and the detection of the second two-dimensional x-ray projection data are carried out during a single passage of a contrast-agent bolus through the breast tissue to be examined. Expressed differently, the recordings of the projection data for the two-dimensional imaging and the three-dimensional imaging are carried out during the passage of one and same contrast-agent bolus. In this way it is possible, firstly, to reduce the examination time of the patient and, secondly, to minimize the strain on the patient by the contrast agent because a renewed administration of a contrast agent is not necessary since both x-ray image recording processes are carried out in one work process.

In a particularly advantageous refinement of the method according to the invention, the first two-dimensional x-ray projection data are detected first and the second two-dimensional x-ray projection data are detected subsequently. That is to say, in this variant the projection data for the two-dimensional imaging of the breast to be examined are detected first and the projection data for the three-dimensional representation of the breast to be examined, generated from the tomosynthesis, are detected subsequently. An advantage of this procedure can be seen in that the first two-dimensional x-ray projection data can be detected at the time of maximum contrast agent accumulation, i.e. 90 to 120 s after the contrast agent administration, in the case where these are used for a two-dimensional high-energy image, contributing to an optimized contrast of the high-energy image.

Within the scope of a preferred variant of the method according to the invention for generating contrast-enhanced image data of breast tissue to be examined, the first two-dimensional x-ray image recording is carried out grid-free without the use of a stray beam grating. The compression of the breast to be examined already leads to a significant reduction in the stray beams, and so an additional absorption of the stray beams is not necessary in the method according to the invention. In particular, a grid-free image data recording is possible if a correction of the x-ray image recordings is carried out with the aid of image correction software in the method according to the invention, wherein interference effects by stray beams are eliminated. The application of correction software renders it possible to carry out the image recordings grid-free since the image artifacts occurring due to the stray radiation can be subsequently removed by calculation with the aid of the correction software. As an additional correction step, a registration of the two image data records to one another can be undertaken prior to the step of subtracting the image data of the synthetic mammogram from the image data of the two-dimensional image data record when generating the two-dimensional dual-energy mammogram.

In a particularly practical variant of the method according to the invention, there is, at a findings workstation, a representation of the two-dimensional dual-energy mammogram and, preferably, of the three-dimensional tomosynthesis image data record as well. Here, the two images can be displayed and observed next to one another, for example on two monitors, or, alternatively, in a manner offset in time.

In a special variant of the method according to the invention, an AEC recording is carried out prior to the first two-dimensional x-ray image recording and recording parameters for the recording of the first two-dimensional projection data and the recording of the second two-dimensional x-ray projection data are established from the AEC recording. Here, an AEC (automatic exposure control) recording should be understood to mean a recording for setting the maximum radiation dose to be used in the following recordings. Here, an x-ray recording of the region to be examined is carried out with a low dose with a resolution in the super-pixel range. On the basis of this advance recording, maximum values for parameters of the x-ray source, such as e.g. the x-ray energy (kV), the amount of radiation (mAs) and the anode filter combination, are set for the subsequent x-ray recordings.

An AEC recording is usually generated as a two-dimensional x-ray recording in the same direction as the two-dimensional x-ray image recording following later on. Preferably, the maximum recording parameters for the second two-dimensional x-ray projection data are established by extrapolation. The fact that the recording direction when detecting the second two-dimensional x-ray projection data varies is taken into account when setting the aforementioned recording parameters for each individual angle by extrapolation. In this manner, it is possible to dispense with additional AEC recordings for the x-ray image recordings for the tomosynthesis, leading to an acceleration of the examination of the patient and, hence, to improved comfort for the patient and a slightly lower exposure in terms of dose of the patient.

In one refinement of the image generation system according to the invention, the projection data acquisition unit comprises a mammogram recording unit and a tomosynthesis recording unit and the image generation system comprises a common object fixation unit and a common imaging unit. Thus, the different x-ray image recordings are preferably carried out by one multi-functional recording device such that the examination position of the breast only needs to be fixed once and can then be maintained for the whole examination.

Other features which are considered as characteristic for the invention are set forth in the appended claims.

Although the invention is illustrated and described herein as embodied in a method and device for generating contrast-enhanced image data of breast tissue to be examined, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Referring now to the figures of the drawing in detail and first, particularly, to FIG. 1 thereof, there is shown a system 10 for two-dimensional x-ray imaging of the breast, which is also referred to as a mammography system. The mammography system 10 comprises an x-ray source 1, from which x-ray radiation 2 is emitted in the direction of a breast 4 in a fan-like manner, i.e. in a beam which widens in a direction orthogonal to the propagation direction. The breast 4 lies on an object table 5 and is pressed against the object table by a compression plate 3. In this way, the thickness of the breast is reduced in the propagation direction of the x-ray radiation, i.e. in the z-direction. The reduction of the object transilluminated by the x-ray radiation is accompanied by a reduction in the stray radiation. Some of the x-ray radiation incident on the breast 4 is absorbed. The rest of the x-ray radiation incident on the breast 4 is transmitted and detected by an image sensor 6.

FIG. 2 shows a conventional tomosynthesis system 20 for three-dimensional x-ray image recording of a breast 4. Unlike the 2D mammography system 10 shown in FIG. 1, the tomosynthesis system comprises an x-ray source 1 that is rotatable or pivotable about the object center M. This allows the x-ray source to take x-ray image recordings of the breast 4 from different directions or angles. The tomosynthesis system 20 shown in FIG. 2 also comprises a compression plate 3, which presses the breast 4 to be examined against an object table 5. The breast 4 to be examined is irradiated by the x-ray source 1 from different angles, with a multiplicity of individual images of the breast 4 being detected by an x-ray detector 6. A three-dimensional slice image which enables a slice-by-slice examination of the tissue of the breast 4, is calculated from the individual images.

Figure 3:
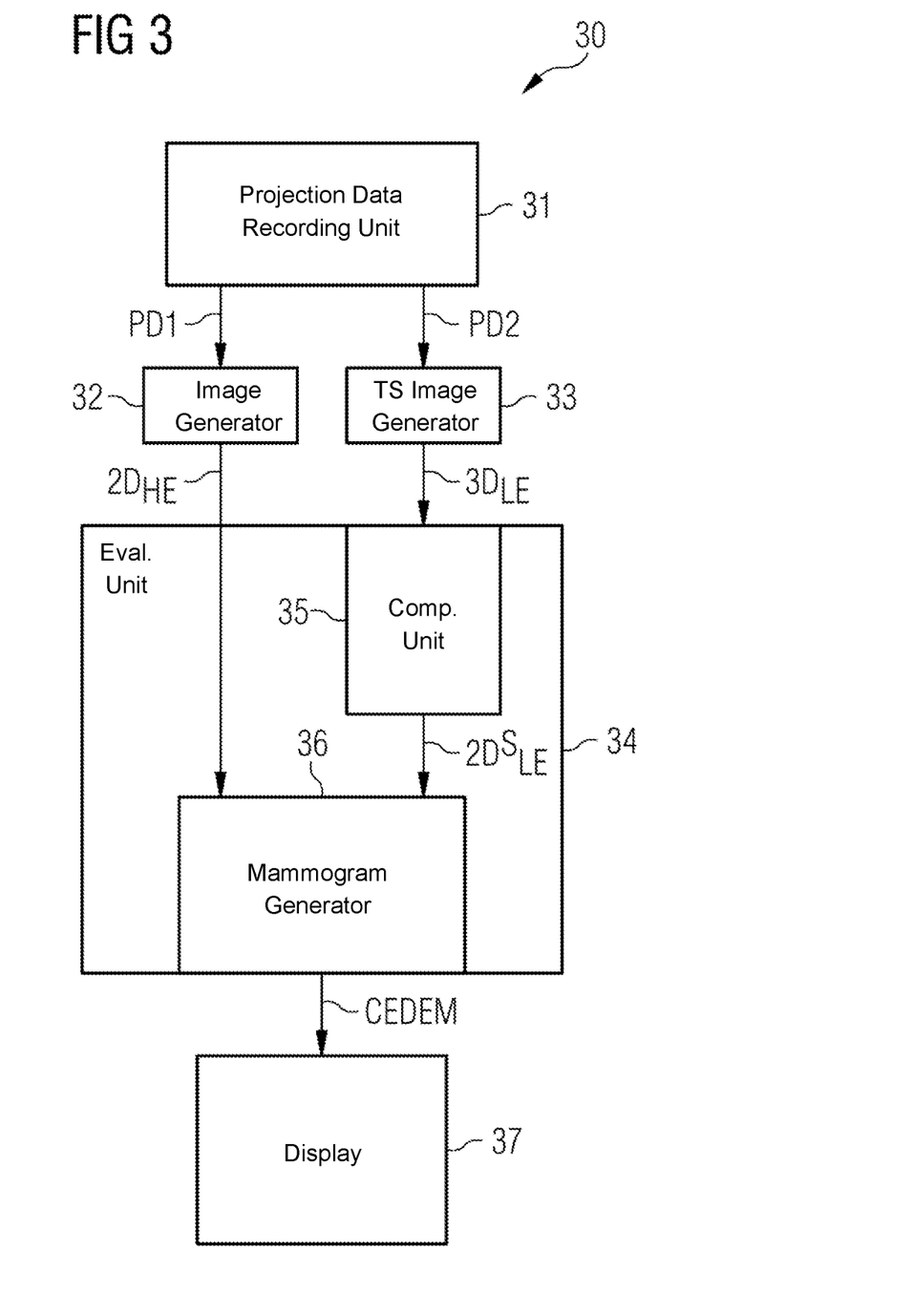
FIG. 3 shows a block diagram, which represents an image data generation system in accordance with an exemplary embodiment of the invention.

FIG. 3 schematically depicts an image data generation system 30 in accordance with one exemplary embodiment of the invention. An x-ray projection data recording unit 31 is part of the image data generation system 30. The x-ray projection data recording unit 31 comprises functional units which render it possible to detect both first projection data PD1 for a two-dimensional high-energy x-ray image recording 2DHE and second projection data PD2 for a three-dimensional low-energy x-ray image recording 3DLE of the female breast. Thus, for example, these functional units can comprise a mammography system 10 and a tomosynthesis system 20, as are depicted in FIG. 1 and FIG. 2.

The first projection data PD1 detected by the x-ray projection data recording unit 31 are transferred to an image data generation unit 32, or image generator, for short. On the basis of the detected first two-dimensional x-ray projection data PD1, the image data generation unit 32 generates a two-dimensional image data record $2D_{HE}$. By way of example, the projection data PD1 are processed by means of a correction program in order to eliminate interference effects which are generated by stray beams.

The second projection data PD2 detected by the x-ray projection data recording unit 31 are transferred to a tomosynthesis image data generation unit 33, or TS image generator, for short. From the detected second two-dimensional x-ray projection data PD2, the tomosynthesis image data generation unit 33 reconstructs a three-dimensional tomosynthesis image data record $3D_{LE}$ of the breast tissue to be examined. In the reconstruction, use can be made, for example, of a reconstruction method based on filtered back projection.

The established image data records $2D_{HE}$, $3D_{LE}$ are transferred to an evaluation unit 34. The evaluation unit 34 comprises a computer unit 35 and a mammogram establishment unit 36, or mammogram generator, for short. By way of example, a process unit can be part of the computer unit 35, by means of which process unit a two-dimensional synthetic mammogram $2D^S_{LE}$ is calculated on the basis of the detected three-dimensional low-energy tomosynthesis recording $3D_{LE}$. Subsequently, the synthetic image information $2D^S_{LE}$ is forwarded to the mammogram establishment unit 36. The mammogram establishment unit 36 moreover obtains image information in relation to the two-dimensional high-energy x-ray image recording $2D_{HE}$ from the image data generation unit 32. Then, by weighted subtraction of the image information of the synthetic mammogram $2D^S_{LE}$ from the image information of the recorded two-dimensional high-energy x-ray image recording $2D_{HE}$, the mammogram establishment unit 36 calculates a two-dimensional dual-energy mammography representation CEDEM from the received image information $2D^S_{LE}$, $2D_{HE}$. The established image data CEDEM are finally transferred to an image representation unit 37, which, by way of example, comprises a screen for the graphical representation of the established image data CEDEM. Additionally, the three-dimensional low-energy tomosynthesis recording $3D_{LE}$ can also be transferred to the image representation unit 37. By way of example, said low-energy tomosynthesis recording can be depicted on a screen of the image representation unit 37 at the same time as the two-dimensional dual-energy mammography representation CEDEM. Alternatively, the two different representations $3D_{LE}$, CEDEM can also be depicted with a time offset on one screen of the image representation unit 37.

Figure 4:
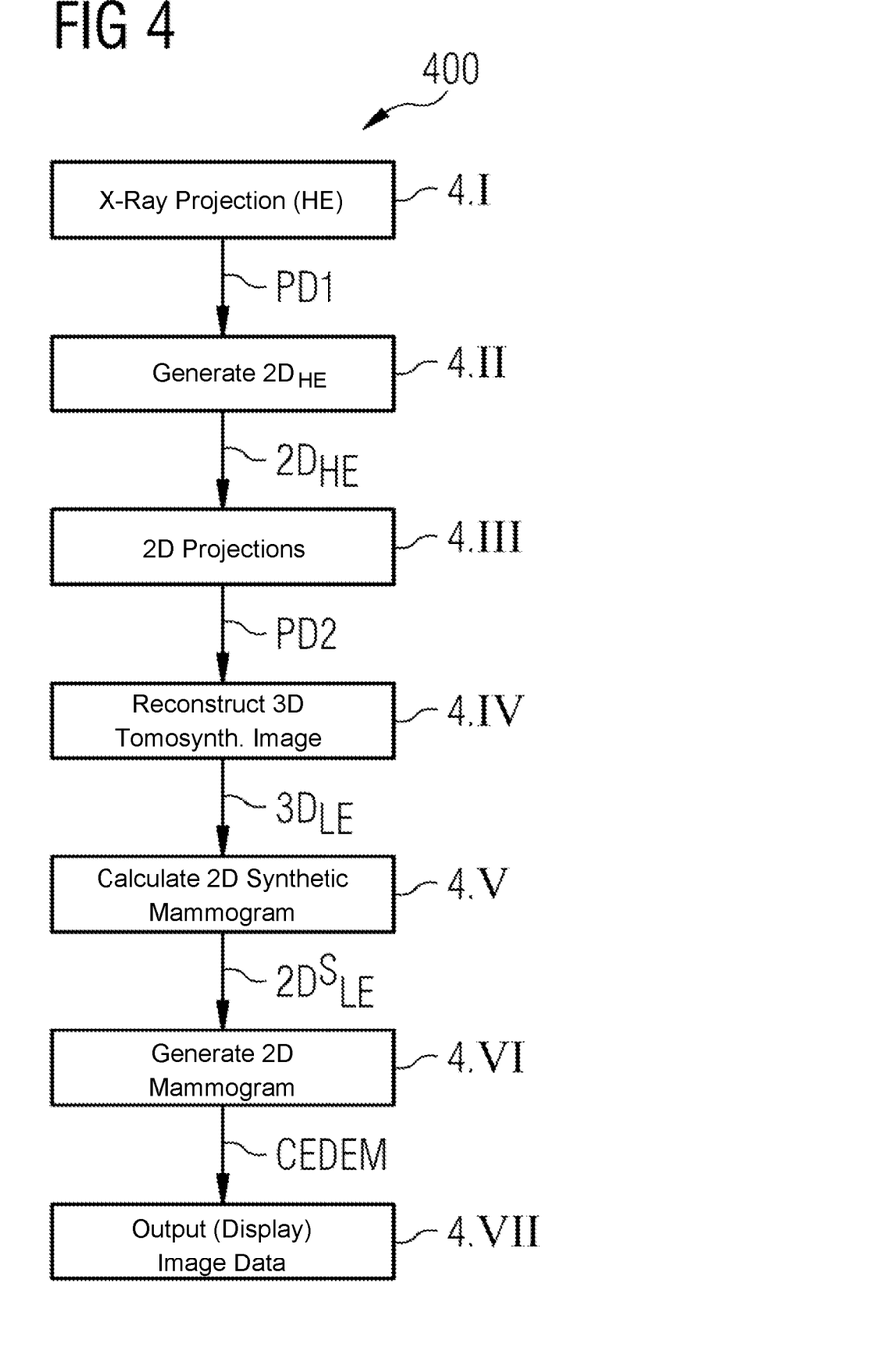
FIG. 4 shows a flowchart which elucidates a method for generating contrast-enhanced image data of breast tissue to be examined in accordance with one exemplary embodiment of the invention.

FIG. 4 shows a flowchart 400, by means of which a method for generating contrast-enhanced image data of breast tissue to be examined is elucidated. Usually, a contrast agent is injected into the bloodstream of a patient prior to the start of the imaging method. The contrast agent also reaches the breast via the blood vessels. Blood vessels are situated in the breast predominantly at the positions at which lesions are present. In this step 4.I, the first two-dimensional x-ray projection data PD1 of the breast tissue to be examined are detected at a higher x-ray beam energy, i.e. at an x-ray beam energy which lies above the absorption edge for x-ray beams of the contrast agent. A two-dimensional image data record $2D_{HE}$ is generated from the detected first two-dimensional x-ray projection data PD1 in step 4.II. Moreover, second two-dimensional x-ray projection data PD2 at a lower x-ray beam energy are detected from different projection angles in step 4.III. In this context, a lower x-ray beam energy should be understood to mean an energy value which lies below the absorption edge for x-ray beams of the contrast agent. Advantageously, steps 4.I to 4.III are carried out in a single workflow, i.e., in particular, without washing-out of the contrast agent and a renewed injection of the contrast agent between the individual image recordings. The three-dimensional tomosynthesis image data record $3D_{LE}$ is reconstructed from the detected second two-dimensional x-ray projection data PD2 in step 4.IV.

Thereupon, a two-dimensional synthetic mammogram $2D^S_{LE}$ is calculated on the basis of the three-dimensional low-energy tomosynthesis recordings $3D_{LE}$ in step 4.V. Subsequently, in step 4.VI, a two-dimensional mammography representation CEDEM with two energies is established by weighted subtraction of the image intensity values $I(2D^S_{LE})$ of the synthetic mammogram $2D^S_{LE}$ from the image intensity values $I(2D^S_{LE})$ of the recorded two-dimensional high-energy x-ray image recording $2D_{HE}$:

$$I(CEDEM)=I(2D_{HE})-\mu*I(2D^S_{LE}), \qquad (1)$$

where the parameter $\mu$ represents a weighting factor which is selected in a manner dependent on the thickness and the tissue density of the breast to be examined.

Finally, in step 4.VII, the established image data CEDEM are depicted graphically on a screen and made available for breast cancer diagnosis.

In conclusion, reference is once again made to the fact that the above-described methods and devices are merely preferred exemplary embodiments of the invention and that the invention can be varied by a person skilled in the art without departing from the scope of the invention, to the extent that the latter is predetermined by the claims. For example, the method and the image data generation system were explained predominantly on the basis of a system for recording medical image data. However, the invention is not restricted to an application in the medical field; instead, the invention can also, as a matter of principle, be applied to recording images for different purposes. Furthermore, the method according to the invention was described in the context of the recording of a two-dimensional mammogram with x-ray radiation at a high energy and the recording of a three-dimensional tomosynthesis image with x-ray radiation at a relatively low energy. It goes without saying that the invention also comprises the reverse case, in which the recording of a two-dimensional mammogram is carried out with x-ray radiation at a relatively low energy and the recording of a three-dimensional tomosynthesis image is carried out with x-ray radiation at a high energy. In this context, the terms "high" and "low" should once again be understood as relative to the energy of the x-ray edge of a contrast agent administered in advance. For the sake of completeness, reference is also made to the fact that the use of the indefinite article "a" or "an" does not preclude the relevant features from also being present multiple times. Likewise, the term "unit" does not preclude that the latter consists of a plurality of components which, where necessary, may also be distributed in space.

The following is a summary list of reference numerals and the corresponding structure used in the above description of the invention:
  1 X-ray source
  2 X-ray radiation
  3 Compression plate
  4 Breast
  5 Object table
  6 Image sensor
  10 Mammography system
  20 Tomosynthesis system
  30 Image data generation system
  31 X-ray projection data recording unit
  32 Image data generation unit
  33 Tomosynthesis image data generation unit
  34 Evaluation unit
  35 Computer unit
  36 Mammogram establishment unit
  37 Image representation unit
  $2D_{HE}$ Two-dimensional high-energy x-ray image recording
  $2D^S_{LE}$ Two-dimensional synthetic mammogram
  $3D_{LE}$ Three-dimensional low-energy/standard energy x-ray image recording
  CEDEM Contrast-agent-enhanced dual-energy mammography representation
  M Object center
  PD1 First two-dimensional x-ray projection data
  PD2 Second two-dimensional x-ray projection data

The invention claimed is:
1. A method of generating contrast-enhanced image data of breast tissue to be examined, the method comprising the following steps:
  detecting a first two-dimensional contrast-agent-influenced x-ray projection data of the breast tissue to be examined at a first x-ray beam energy;
  generating a two-dimensional image data record based on the first two-dimensional x-ray projection data;
  detecting from a plurality of different projection angles a second two-dimensional contrast-agent-influenced x-ray projection data at a second x-ray beam energy that differs from the first x-ray beam energy;
  reconstructing a three-dimensional tomosynthesis image data record of the breast tissue to be examined from the detected second two-dimensional x-ray projection data;
  calculating a two-dimensional synthetic mammogram based on the three-dimensional tomosynthesis image data record reconstructed from the x-ray projection data from the plurality of different projection angles;
  establishing a two-dimensional dual-energy mammogram by subtracting the image data of the synthetic mammogram from the image data of the two-dimensional image data record;
  wherein: the first x-ray beam energy has an energy value which lies above an x-ray edge of a contrast agent applied for contrast enhancement and the second x-ray beam energy has an energy value which lies below the x-ray edge of the contrast agent applied for contrast enhancement; or the first x-ray beam energy has an energy value which lies below the x-ray edge of the contrast agent applied for contrast enhancement and the second x-ray beam energy has an energy value which lies above the x-ray edge of the contrast agent applied for contrast enhancement.

2. The method according to claim 1, which comprises first detecting the first two-dimensional x-ray projection data and subsequently detecting the second two-dimensional x-ray projection data.

3. The method according to claim 1, wherein the step of subtracting the image data comprises subtracting weighted image intensities of the two image data records.

4. The method according to claim 3, which comprises setting the weighting of the image intensities such that background image data of the two image data records are eliminated.

5. The method according to claim 1, which comprises detecting the first two-dimensional x-ray projection data and detecting the second two-dimensional x-ray projection data during a single workflow while maintaining a breast compression and/or while maintaining a position of the breast.

6. The method according to claim 5, which comprises detecting the first two-dimensional x-ray projection data and detecting the second two-dimensional x-ray projection data during a single passage of a contrast-agent bolus through the breast tissue to be examined.

7. The method according to claim 1, which comprises recording a first two-dimensional x-ray image at the first x-ray beam energy for detecting the first two-dimensional x-ray projection data and recording a plurality of second two-dimensional x-ray images from a plurality of different angles at the second x-ray beam energy for detecting the second two-dimensional x-ray projection data.

8. The method according to claim 7, which comprises, prior to detecting the first x-ray projection data, carrying out an automatic exposure control (AEC) recording and establishing recording parameters for the recording of the first two-dimensional x-ray projection data and the recording of the second two-dimensional x-ray projection data on a basis of the AEC recording.

9. The method according to claim 7, which comprises representing the two-dimensional dual-energy mammogram at a findings workstation.

10. The method according to claim 9, which comprises also representing the three-dimensional tomosynthesis image data record at the findings workstation.

11. The method according to claim 7, which comprises carrying out an image correction of the first two-dimensional x-ray image by employing image correction software.

12. The method according to claim 11, which comprises establishing recording parameters for the second two-dimensional x-ray projection data by extrapolation.

13. A computer program product comprising a computer program in non-transitory form to be loaded directly into a memory unit of an image data generation system, the computer program comprising program code for executing the method according to claim 1 when the computer program is executed in the image data generation system.

14. A computer-readable medium having stored thereon program portions in non-transitory form which are able to be read and executed by a processing unit of an image data generation system, the program portions comprising program code for executing the method according to claim 1 when the computer code is executed in the image data generation system.

* * * * *